United States Patent
Scofield

(10) Patent No.: US 9,174,156 B2
(45) Date of Patent: Nov. 3, 2015

(54) SYSTEM FOR DETERMINING FORCE IMPARTED BY A FILTER IN A VARIABLE FORCE ENVIRONMENT AND RELATED METHODS OF USE

(71) Applicant: Magni-Power Company, Wooster, OH (US)

(72) Inventor: William H. Scofield, Batavia, IL (US)

(73) Assignee: Magni-Power Company, Wooster, OH (US)

( * ) Notice: Subject to any disclaimer, the term of this patent is extended or adjusted under 35 U.S.C. 154(b) by 0 days.

(21) Appl. No.: 14/678,802

(22) Filed: Apr. 3, 2015

(65) Prior Publication Data

US 2015/0285517 A1    Oct. 8, 2015

Related U.S. Application Data

(60) Provisional application No. 61/975,463, filed on Apr. 4, 2014.

(51) Int. Cl.
| | | |
|---|---|---|
| *B01D 46/00* | (2006.01) | |
| *F24F 3/16* | (2006.01) | |
| *B01D 46/44* | (2006.01) | |
| *G01N 15/08* | (2006.01) | |

(52) U.S. Cl.
CPC ............ *B01D 46/0086* (2013.01); *B01D 46/44* (2013.01); *F24F 3/1603* (2013.01); *G01N 15/082* (2013.01); *F24F 2003/1614* (2013.01); *G01N 2015/084* (2013.01)

(58) Field of Classification Search
CPC .. B01D 46/0086; B01D 46/44; B01D 46/446; F24F 3/1603; F24F 2003/1614
See application file for complete search history.

(56) References Cited

U.S. PATENT DOCUMENTS

| | | |
|---|---|---|
| 3,928,006 A | 12/1975 | Martineau |
| 6,168,646 B1 | 1/2001 | Craig et al. |
| 6,413,290 B1 | 7/2002 | Gruber |
| 6,443,010 B1 | 9/2002 | Scofield |
| 6,734,801 B2 | 5/2004 | Scofield |
| 7,594,960 B2 | 9/2009 | Johansson |
| 7,713,339 B2 | 5/2010 | Johansson |
| 8,704,672 B2 | 4/2014 | Hoglund et al. |
| 2011/0132816 A1 | 6/2011 | Vasilescu |
| 2012/0323375 A1* | 12/2012 | Dean-Hendricks et al. .. 700/276 |
| 2013/0276629 A1* | 10/2013 | Salahshour et al. ............. 95/25 |

FOREIGN PATENT DOCUMENTS

KR    20060041379    5/2006

OTHER PUBLICATIONS

Gibson, David, "Variable Frequency Drives (VFDs): Energy Efficiency Opportunities," Ameren Illinois, (12 pages).

* cited by examiner

*Primary Examiner* — Robert Clemente
(74) *Attorney, Agent, or Firm* — Bookoff McAndrews, PLLC

(57) ABSTRACT

A control system for a variable flow filtration system that is configured for receiving an operating condition of a variable speed impeller of the variable flow filtration system; determining a threshold filter force associated with the received operating condition to determine an increased threshold filter force proportionally to increases in the received operating condition; receiving one or more real-time environmental conditions of the variable flow filtration system; modifying the determined threshold filter force based on the received one or more real-time environmental conditions; receiving a real-time filter force imparted by a filter of the variable flow filtration system on a load cell or other filtration system component, the filter force being imparted by a flow of gas or fluid driven by the variable speed impeller; comparing the received real-time filter force to the modified determined threshold filter force; and generating a filter status notification based on the comparison.

20 Claims, 16 Drawing Sheets

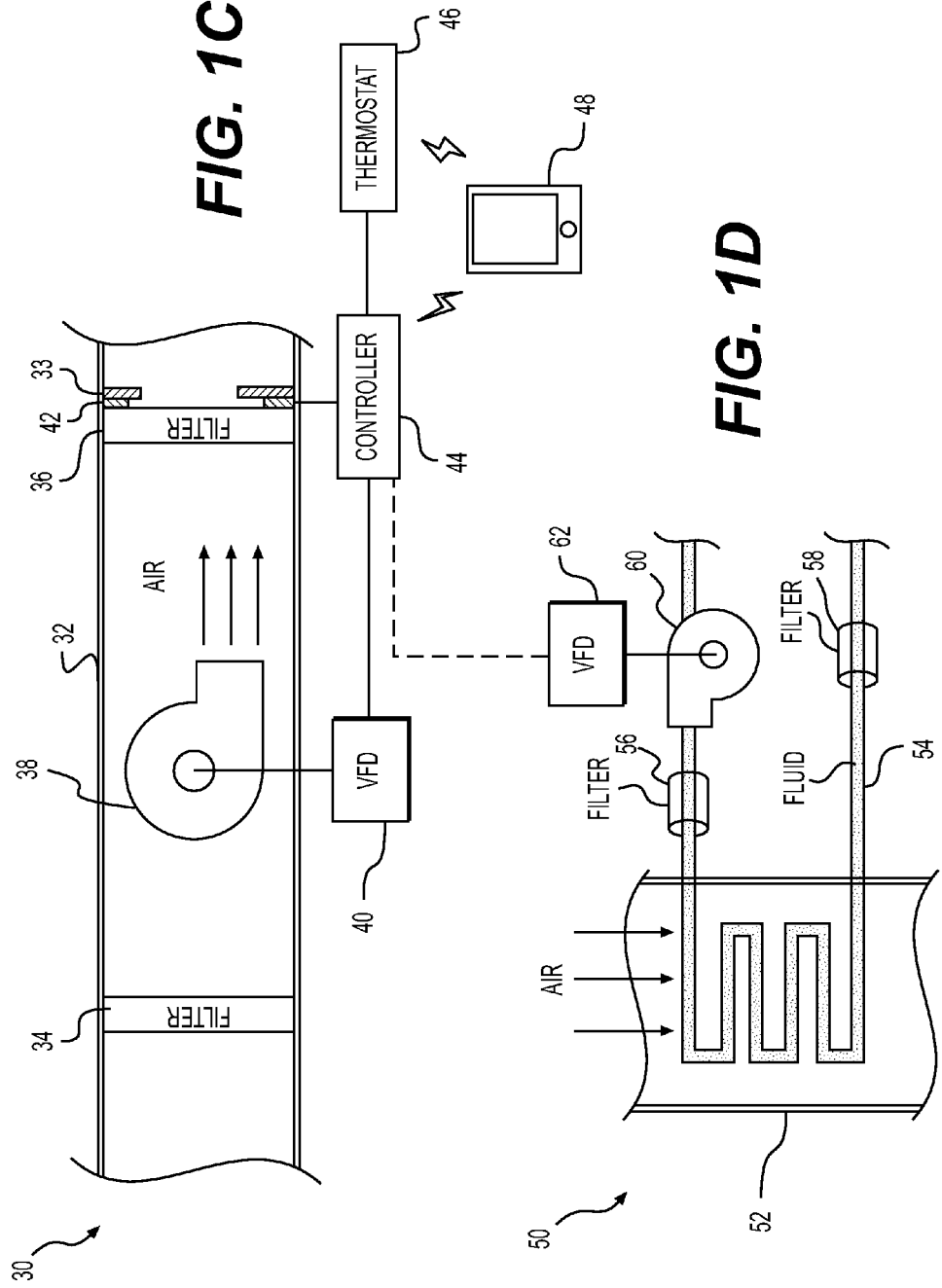

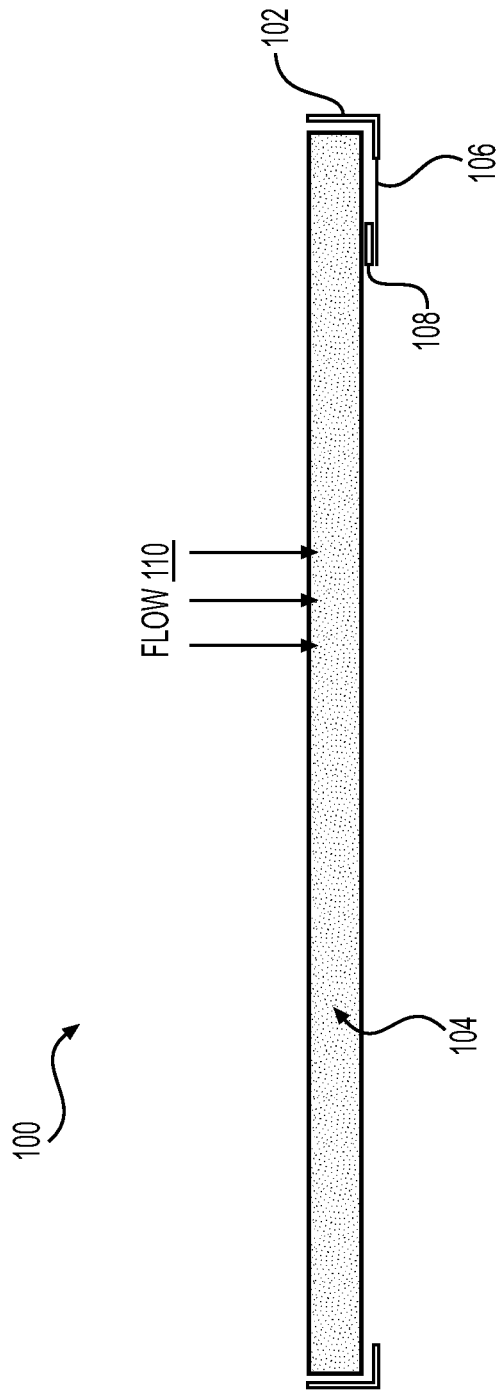

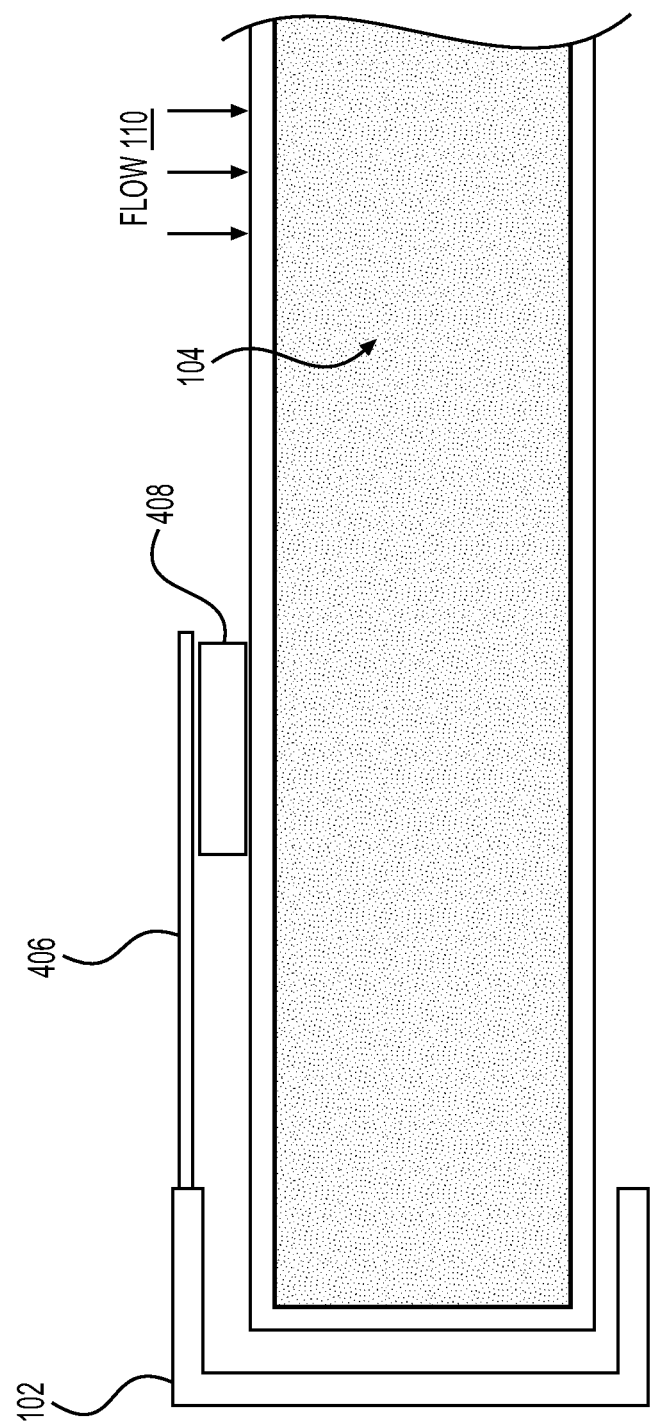

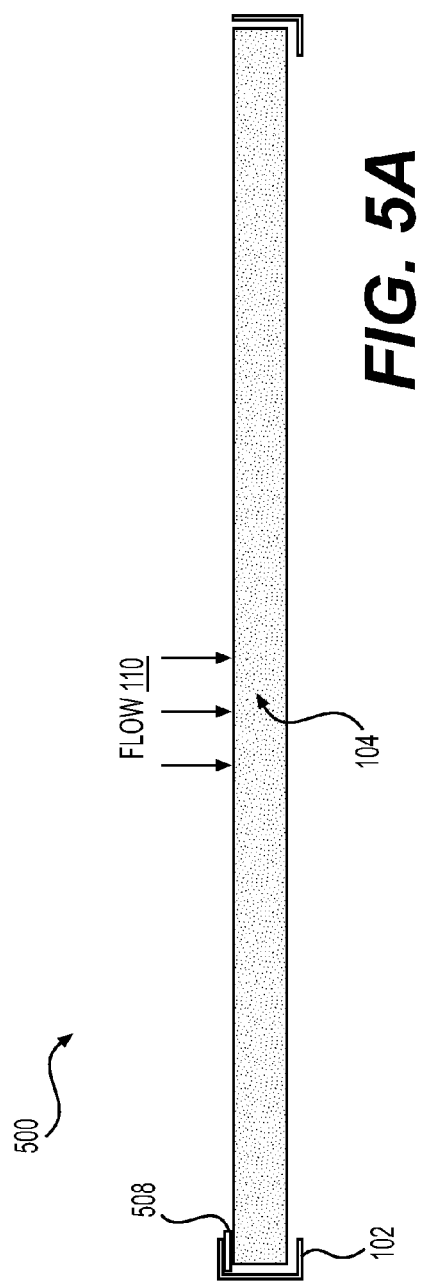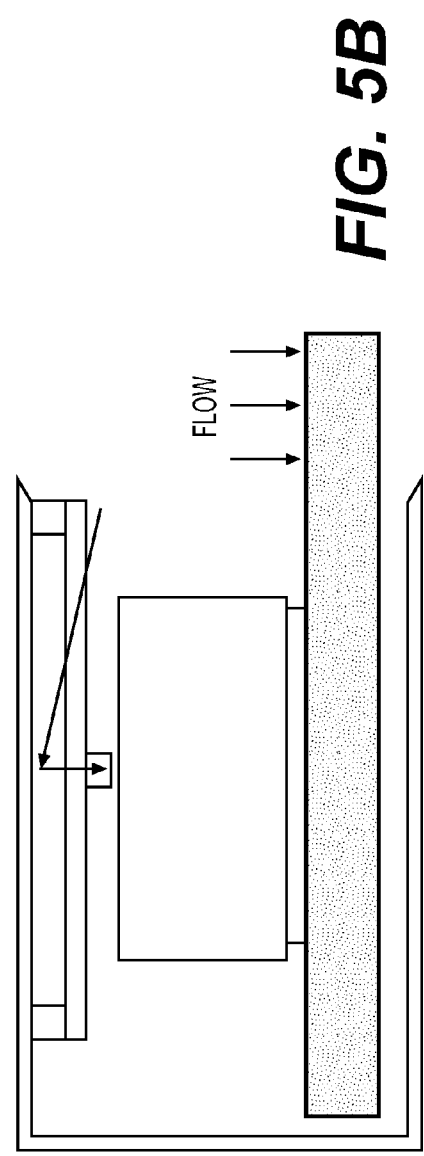

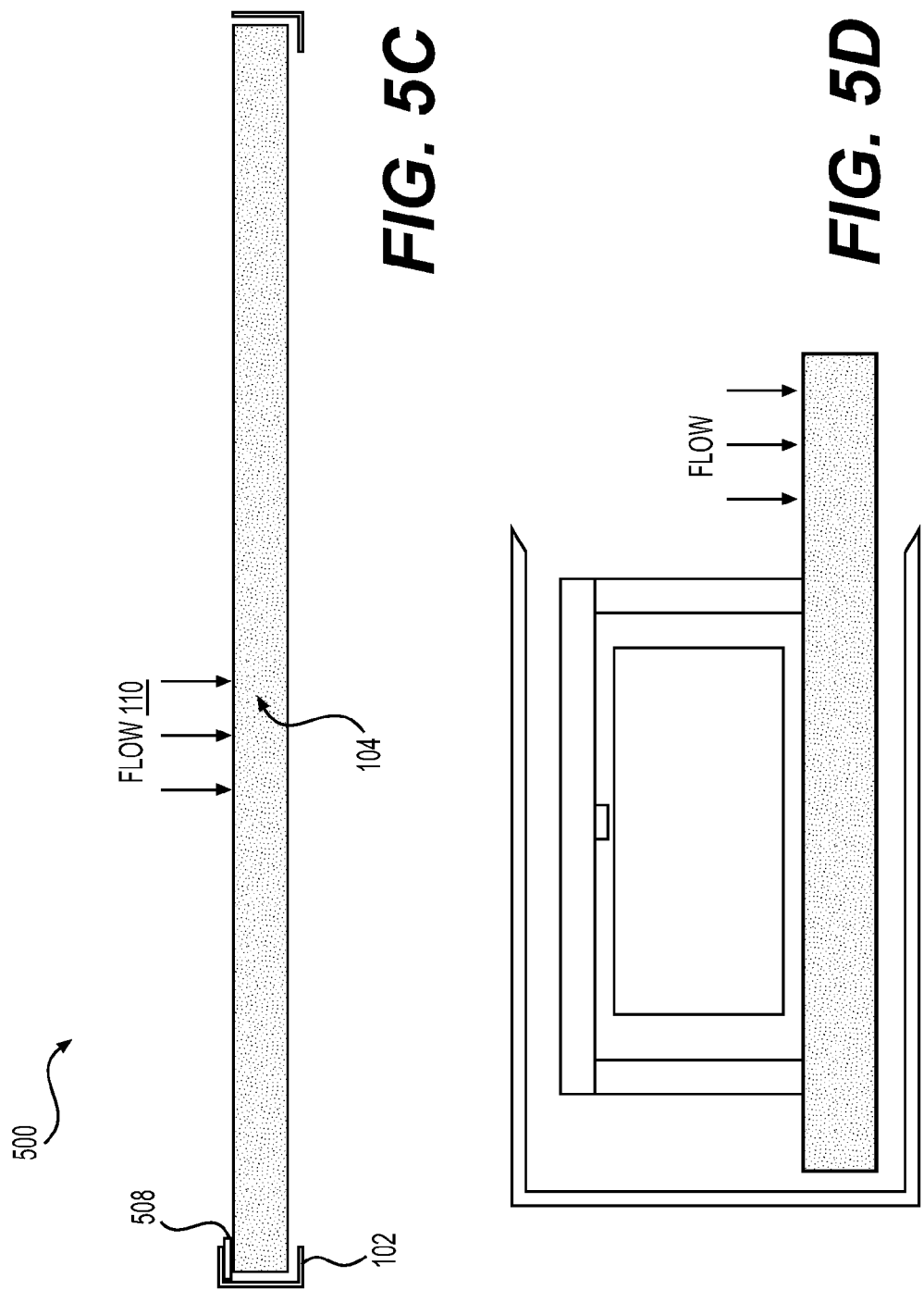

SYSTEM FOR DETERMINING FORCE IMPARTED BY A FILTER IN A VARIABLE FORCE ENVIRONMENT AND RELATED METHODS OF USE

RELATED APPLICATIONS

This application claims priority to U.S. Provisional Application No. 61/975,463 filed Apr. 4, 2014, the entire disclosure of which is hereby incorporated herein by reference in its entirety.

TECHNICAL FIELD

Various embodiments of the present disclosure relate generally to a filtration system. More specifically, exemplary embodiments of the present disclosure relate to filter systems and methods for determining a loading condition of a filter in a variable flow environment.

BACKGROUND

Filtration is a ubiquitous technique used for removing particulates and other unwanted matter from any type of fluid or gas. For example, in many heating, ventilation and air conditioning (HVAC) systems, air (and other fluids and gasses) are filtered to remove debris within an enclosed space of a temperature-controlled environment. In the case of HVAC systems, for example, as the air is circulated, an air filter collects and traps particulate matter which is later removed via either filter replacement or cleaning. A dirty or loaded air filter places a strain on the air movers of the HVAC system, which can cause increased power consumption, reduced airflow, mechanical stress on the motors of the air movers, and shorter system life expectancy. In some instances, air filters are physically inspected to determine if maintenance or replacement is necessary. In other instances, air filters are replaced at scheduled intervals, even if the air filter does not necessarily need to be changed. Often, air filter replacement and/or cleaning does not take place at proper intervals, and overall system performance is negatively impacted.

Likewise, liquid and gas filtering systems are an integral component in the gas and oil industry, and in other systems that involve the removal of contaminants from a flowing stream of liquids and gases. For example, in automotive and industrial applications, fluid filters are used to remove particulates from motor oils (e.g., using an oil filter), refrigerants, coolants, and brake fluids. In the case of industrial applications, many companies spend significant time and resources on monitoring, scheduling, and replacing dirty oil and coolant filters, and on repairing damage that occurs from overly dirty fluid filters.

Moreover, the nature of filtration is changing due to the changing nature of forced fluids and air systems. In particular, whereas in the past, air and fluids were either being driven, or not, in modern systems, air and fluids are more often being driven at variable speeds and forces. As a result, existing techniques are insufficient for determining filter loading by measuring an amount or extent of clogging or dirtiness.

Accordingly, a need exists for a system to accurately determine the status of filters by determining an amount or extent of clogging or dirtiness of fluid/air filters in a variable flow environment.

SUMMARY OF THE DISCLOSURE

According to certain embodiments, systems and methods are disclosed for determining force acting on a filter and related methods of use.

In one aspect, the present disclosure is directed to a filter system. The filter system may include a housing, and a filter media supported by the housing. The filter system may also include a sensor coupled to the filter media to measure a force exerted by the filter media.

Various examples of the present disclosure may include one or more of the following features: wherein the sensor may be mounted at a downstream surface of the filter media; wherein the sensor may be configured to measure a compressive force exerted by the media; wherein the sensor may be mounted at an upstream surface of the filter media; wherein the sensor may be configured to measure a tensile force exerted by the filter media; wherein sensor may be configured to measure two or more forces exerted by the filter media in different directions; further including a receiver that may be in communication with the sensor; wherein the sensor may communicate a loading condition of the filter to the receiver.

In another aspect, the present disclosure may be directed to a filter for use with an HVAC system. The filter may include a housing disposed with a duct of the HVAC system, and a filter media supported by the housing. The filter may also include a sensor coupled to the filter media to measure a force exerted by the filter media, and a receiver in communication with the sensor. The sensor may be configured to communicate the measured force to the receiver, and the measured force may be indicative of a loading condition of the filter media.

In one aspect, the present disclosure is directed to a computer-implemented method of generating a filter status notification or signal of a filter in a variable flow environment, the computer-implemented method comprising: receiving an operating condition including one or more of a fan setting, a pump setting, an intensity setting, a fan speed, a rotational velocity, a voltage, a current, an air/fluid flow rate, and a force associated with a variable speed impeller of a filtration system; determining a threshold filter force associated with the received operating condition to determine an increased threshold filter force proportionally to increases in one or more of the fan setting, the pump setting, the intensity setting, the fan speed, the rotational velocity, the voltage, the current, the air/fluid flow rate, and the force associated with the variable speed impeller of the filtration system; receiving one or more real-time environmental conditions including one or more of a temperature measurement, a humidity measurement, an air or fluid density measurement, an altitude measurement, and an air or fluid pressure measurement of the filtration system; modifying the determined threshold filter force based on the received one or more real-time environmental conditions (i) to decrease the determined threshold filter force proportionally to increases in the temperature measurement and/or proportionally to increases in the altitude measurement; and (ii) to increase the determined threshold filter force proportionally to increases in the humidity measurement, to increases in the air or fluid density measurement, and/or to increases in the air or fluid pressure measurement of the filtration system; receiving, from a load cell, a real-time filter force imparted by a filter of the filtration system on the load cell and/or a component of the filtration system, the force of the filter on the component being imparted by a flow of gas or fluid driven by the variable speed impeller; comparing the received real-time filter force to the modified determined threshold filter force; and generating a filter status notification or signal based on the comparison of the real-time filter force to the determined threshold filter force.

In one aspect, the present disclosure is directed to a control system for a variable flow filtration system, the control system comprising: a digital data storage device storing instructions for generating a filter status notification or signal; and a processor configured to execute the stored instructions to perform a method comprising: receiving, from a variable speed impeller of the variable flow filtration system, an operating condition of the variable speed impeller of the filtration system; determining a threshold filter force associated with the received operating condition to determine an increased threshold filter force proportionally to increases in the received operating condition; receiving one or more real-time environmental conditions of the variable flow filtration system; modifying the determined threshold filter force based on the received one or more real-time environmental conditions; receiving, from a load cell, a real-time filter force imparted by a filter of the variable flow filtration system on the load cell or on a component of the variable flow filtration system, the force of the filter being imparted by a flow of gas or fluid driven by the variable speed impeller; comparing the received real-time filter force to the modified determined threshold filter force; and generating a filter status notification or signal based on the comparison of the real-time filter force to the determined threshold filter force.

In one aspect, the present disclosure is directed to a variable flow filtration system comprising a filter disposed across a flow of fluid or gas; a load cell disposed between the filter and a component of the variable flow filtration system; a variable speed impeller configured to drive fluid or gas through the filter of the variable flow filtration system; and a controller. The controller is configured to: receive, from the variable speed impeller of the variable flow filtration system, an operating condition of the variable speed impeller of the filtration system; determine a threshold filter force associated with the received operating condition to determine an increased threshold filter force proportionally to increases in the received operating condition; receive one or more real-time environmental conditions of the variable flow filtration system; modify the determined threshold filter force based on the received one or more real-time environmental conditions; receive, from the load cell, a real-time filter force imparted by the filter of the variable flow filtration system on the load cell or the component of the variable flow filtration system; compare the received real-time filter force to the modified determined threshold filter force; and generate a filter status notification or signal based on the comparison of the real-time filter force to the determined threshold filter force.

Various examples of the present disclosure may include one or more of the following features: wherein the operating condition is received from the variable speed impeller of the filtration system; wherein the real-time environmental condition is received from a sensor positioned in the filtration system; wherein the received operating condition is received continuously in real-time, the one or more real-time environmental conditions are received continuously in real-time, and the real-time filter force is received from the load cell continuously in real-time; wherein the received operating condition is received at a first predetermined interval, the one or more real-time environmental conditions are received at a second predetermined interval, and the real-time filter force is received from the load cell at a third predetermined interval, wherein the first, second, and third predetermined intervals are different from each other or the same; wherein the one or more operating conditions includes one or more of: a fan setting, a pump setting, an intensity setting, a fan speed, a rotational velocity, a voltage, a current, an air/fluid flow rate, and a force associated with the variable speed impeller of the filtration system; wherein the one or more environmental conditions include one or more of: a temperature measurement, a humidity measurement, an air or fluid density measurement, an altitude measurement, and an air or fluid pressure measurement of the filtration system; wherein modifying the determined threshold filter force based on the received one or more real-time environmental conditions comprises (i) decreasing the determined threshold filter force proportionally to increases in the temperature measurement and/or proportionally to increases in the altitude measurement; and (ii) increasing the determined threshold filter force proportionally to increases in the humidity measurement, to increases in the air or fluid density measurement, and/or to increases in the air or fluid pressure measurement of the filtration system; wherein the load cell is mounted at an upstream or downstream surface of the filter; wherein the load cell is configured to measure a compressive or tensile force exerted by the filter.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIG. 1C is a schematic diagram of an exemplary air flow filtration system and environment in which embodiments of the present disclosure may be practiced;

FIG. 1D is a schematic diagram of an exemplary fluid flow filtration system and environment in which embodiments of the present disclosure may be practiced;

FIGS. 2B and 2C are side view illustrations of the filter system of FIG. 2A;

FIGS. 4A-4B are side view illustrations of another filter system, according to an exemplary embodiment of the present disclosure;

FIGS. 5A-5D are side view illustrations of another filter system, according to an exemplary embodiment of the present disclosure;

DESCRIPTION OF THE EMBODIMENTS

Reference will now be made in detail to the exemplary embodiments of the disclosure, examples of which are illustrated in the accompanying drawings. Wherever possible, the same reference numbers will be used throughout the drawings to refer to the same or like parts.

Figure 1A:
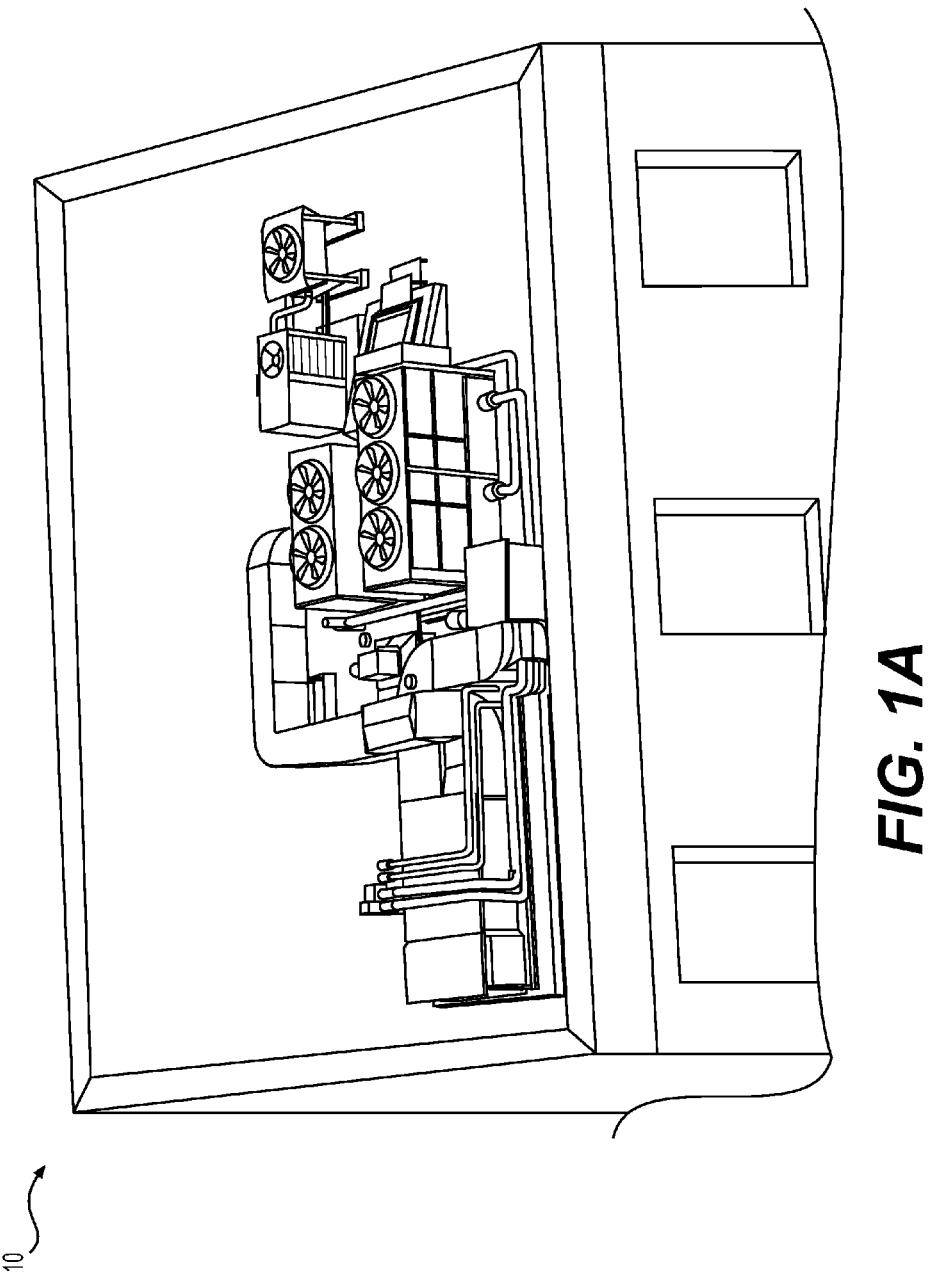
FIG. 1A is a perspective view of an exemplary industrial HVAC system and environment in which embodiments of the present disclosure may be practiced.
Figure 1B:
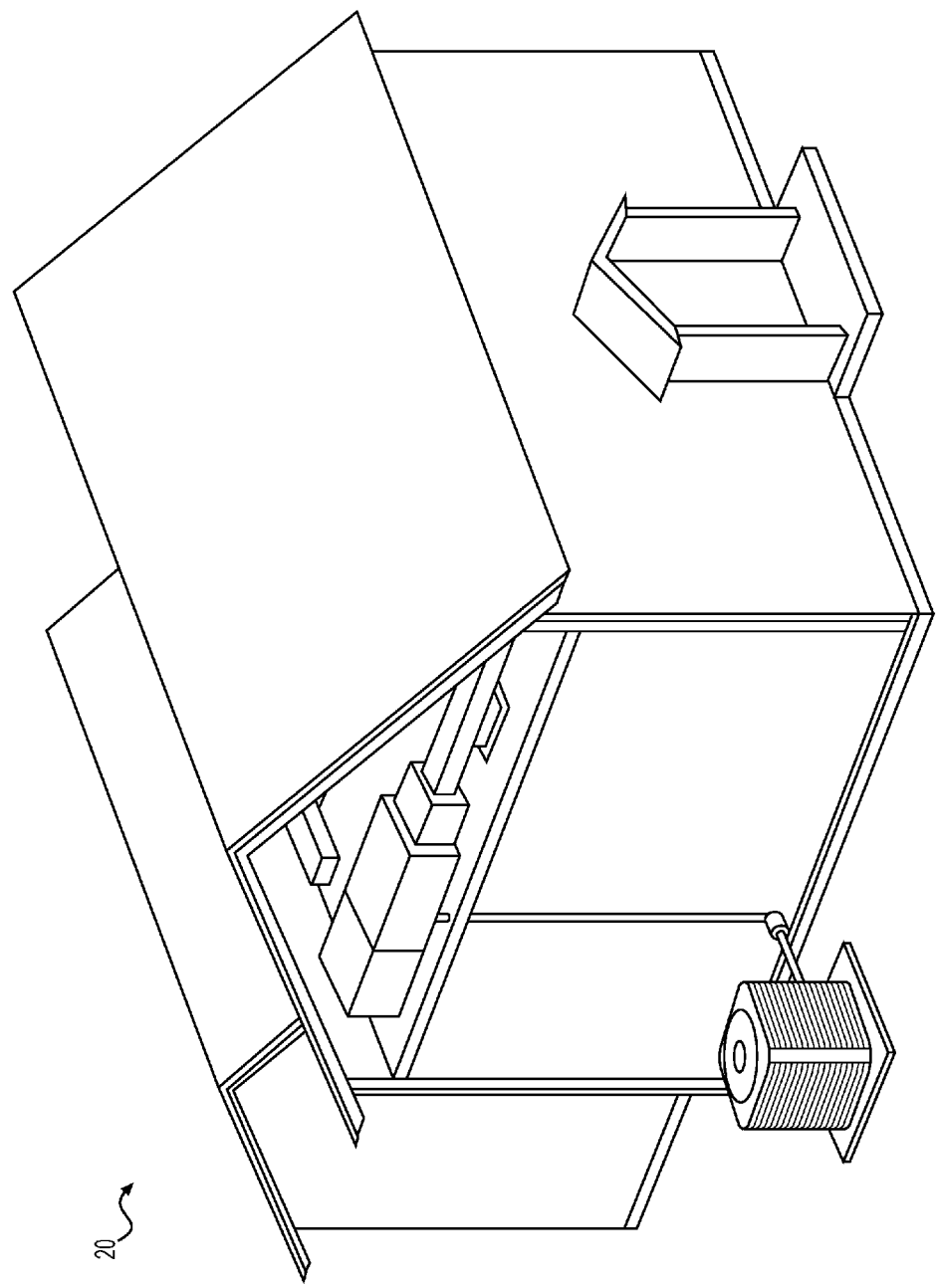
FIG. 1B is a perspective view of an exemplary residential HVAC system and environment in which embodiments of the present disclosure may be practiced.

In general, the present disclosure is directed to systems and methods for determining when a filter of an air or gas/fluid filtration system is dirty and should be changed or cleaned. The present disclosure is applicable to any type of filtration system, including but not limited to HVAC systems, fluid filtering systems, water filtration, oil filtration, or any other application in which a filter is used to capture particulate matter from a flow of air and/or fluid. By way of example, FIG. 1A is a perspective view of an exemplary industrial HVAC system and environment in which embodiments of the present disclosure may be practiced. FIG. 1B is a perspective view of an exemplary residential HVAC system and environment in which embodiments of the present disclosure may be practiced. It should be appreciated that the systems of FIGS. 1A and 1B are merely illustrative in nature, and are not limiting of the present disclosure.

At a high level, the present disclosure describes a system comprising a load sensor positioned in relation to any type of filter, the load sensor being configured to detect and measure an amount or extent of loading or force of the filter on the load sensor and/or on a member or frame proximate to the filter. The load sensor may be any type of transducer configured to create an electrical signal in proportion to a force being measured. By way of example, the load sensor may be a hydraulic load cell or one utilizing hydraulic forces, a pneumatic load cell or one utilizing compressive gaseous forces, a piezoelectric load cell, and/or a strain gauge load cell, pressure sensitive thin film embodiments (such as those used in touch screen applications), laser displacement force measurement devices, and/or linear and non-linear displacement force measurement devices In one embodiment, the load cell may be configured to transmit the amount or extent of loading or force for purposes of a comparison against a variable baseline level of force of the filter, by which the load cell may detect loading and/or force even in cases where the filter media may not necessarily deform at all, or even in cases where the filter media deforms by a relatively small or undetectable amount. For example, whereas in traditional filtration applications a filter may be under a relatively binary distribution of forces (i.e., the blower or pump is either on or off), the filter of the present disclosure may be positioned within a variable speed air or fluid/gas environment. For example, the filtration system consistent with the present disclosure may include a fan, blower, pump, or any other impeller configured to move air, fluid, and/or gas at selectively variable speeds. In one embodiment, the fan, blower, pump, etc. of the present disclosure may be positioned in communication with a variable speed drive. For example, the fan, blower, pump, etc. may be disposed in communication with, and indeed driven by, any desired type of variable-frequency drive (VFD), adjustable-frequency drive (AFD), variable-speed drive (VSD), AD drive, micro drive, inverter drive, or any other type of electro-mechanical drive means that controls a motor speed by varying input frequency, current, and/or voltage.

In one embodiment, the variable speed drive and the load sensor may be provided in communication with a controller that is configured to perform a method of determining an amount or extent of filter loading or clogging. For example, in one embodiment, the controller may be configured to receive a value of operation of a fan or blower of a variable speed filtration (e.g., HVAC or fluid) system. The value of operation of the fan or blower may include one or more of a fan setting, a pump setting, an intensity setting, a fan speed, a rotational velocity, a voltage, a current, an air/fluid flow rate, or a force associated with the fan or blower. Moreover, the value of operation of the fan or blower may include and/or be supplemented by a temperature measurement, a humidity measurement, an air or fluid density measurement, an altitude measurement, an air or fluid pressure measurement. Moreover, the value of operation of the fan or blower may include and/or be supplemented by measurements or parameters associated with changes in height, location, and/or temperature of one or more components of the filtration system. The controller may further be configured to receive, from the load sensor, a value of force of a filter of the filtration system against the load sensor or another member of the filtration system. The controller may further be configured to compare the received value of force of the filter to either the received value of operation of the fan or blower, or a predetermined value of force stored in relation to the value of operation of the fan or blower. Finally, the controller may be configured to determine whether to generate a signal associated with the filter being more loaded, clogged, or dirty, than desired. In one embodiment, the controller may generate a signal associated with the filter being more loaded, clogged, or dirty, than desired, if the received value of force of the filter is outside a threshold value (i.e., below a lower threshold or above an upper threshold) from the received value of operation of the fan or blower, or the predetermined value of force stored in relation to the value of operation of the fan or blower.

It should be appreciated that the arrangement of the load sensor and the filter in communication with the controller may enable detection of increased force even in cases when the filter is not deformed, which may be especially advantageous in scenarios in which filter deformation is especially undesirable. In other words, the presently disclosed systems and methods may involve triggering a signal indicative of filter clogging at a threshold prior to deformation occurring. As described above, the threshold may be dependent on the type of filter media being used. For example, high efficiency filters (often referred to as HEPA filters), which are used to remove the smallest of particulate sizes, exert a greater force in the direction of flow, whereas other filter media designed to capture the larger particulate matter may have a much greater free area ratio. Thus, the presently disclosed arrangement may enable setting a threshold depending on the type of filter media, whether dense to capture small particulate, or very porous, for use in direct correlation to the speed of the flow. For example, if an HVAC system with a HEPA filter involves high volume flow at one point in time, then the force exerted by the filter may be much greater in comparison to a point in time where the required flow rate is much lower. With a known relationship between the free area of the filter, and its inherent ability to restrict flow, and the speed of the air mover, for example, the system may determine a threshold for triggering an indication of filter clogging. With the type of media entered into the controller, in addition to or in alternative to its free area ratio, the controller which receives the output of the force applied by the filter media may determine the appropriate threshold for triggering an alarm, thereby preventing artificial false triggers. For example, if a threshold is set with the flow at ¾ capacity, then a false trigger may occur at high flow due to the inherent higher forces exerted at higher speeds. Additionally, any changes in humidity or density would also impact the forces exerted on the filter. The controller therefore may be configured to gather several environmental conditions to more accurately determine the appropriate threshold.

In one embodiment, for example, if a VFD-driven fan is operating at, for example, 1025 RPM, to drive 78 degree Fahrenheit air into an environment at 72 degrees Fahrenheit, then the tolerable range of filter forces should be 145-155 PSI. If the force of the filter is outside the 145-155 PSI range while the fan is operating within 5-10% of 1025 RPM, then an alarm may be triggered. In some embodiment, a matrix, curve, mapping/map, or look-up table of tolerable forces may be generated and accessed all possible operating conditions and/or environmental conditions of the VFD-driven fan.

It should be appreciated that the presently disclosed systems and methods are advantageously improved over existing systems that are applicable only to particular filtration systems. For example, the presently disclosed systems are applicable not only to air filtration, but also to any flowing gas or liquid. Moreover, the presently disclosed load sensors may be positioned not only downstream from a filter, but alternatively or additionally upstream from a filter, and/or perpendicularly to a fluid/gas flow. Moreover, the presently disclosed load sensors may be used in relation not only to deformable filter media, but also to rigid filter media, and to any shape of filter media. Moreover, the presently disclosed load sensors do not just trigger a dirty filter alarm at a single predetermined load (e.g., akin to on/off switch), but rather they enable a continuum or gradient of loads in varying atmospheric conditions, any of which may trigger different types of alarms or actions, and which may be normalized to account for a particular level and/or direction of air/fluid flow.

FIG. 1C is a schematic diagram of an exemplary air flow HVAC filter system and environment in which embodiments of the present disclosure may be practiced. FIG. 1C depicts an air or gas environment 30, comprising a duct 32 having one or more filters 34, 36 and any type of fluid/gas impeller, e.g., a fan, blower, or pump 38. It should be appreciated that the air or gas environment 30 may include one or more upstream filters 34, one or more downstream filters 36, or both of one or more upstream filters 34 and one or more downstream filters 36. Thus, while FIG. 1C depicts one or more load sensors 42 depicted in relation to a downstream filter 36, as will be described in more detail with respect to the disclosure that follows, the air or gas environment 30 may include one or more load sensors 42 at an upstream filter 34, or at both an upstream filter 34 and a downstream filter 36. Thus, the particular embodiment of FIG. 1C should not be construed as limiting with respect to the arrangement of filters in relation to the duct 32 and/or the fan, blower, or pump 38.

Nevertheless, as shown in FIG. 1C, filter 36 is depicted as being disposed across an air or gas flow through duct 32 and as being supported by one or more framing elements or members 33 of duct 32. Moreover, as shown in FIG. 1C, one or more load sensors 42 are depicted as being disposed between filter 36 and framing elements or members 33 of duct 32. In one embodiment, at least one load sensor 42 is connected to a framing element or member 33 of duct 32 and configured to detect and measure an amount or extent of force that filter 36 applies against the framing element or member 33 through the load sensor. In one embodiment, the load sensor 42 may be configured to detect and measure a portion of the force imparted by filter 36, such as one half, or one quarter of the filter, in cases where an opposing half or quadrant of filter 36 is supported and measured by another load sensor. Alternatively, the load sensor 42 may be configured to detect and measure a substantial majority component, or even all of a force imparted by a filter against a framing element or member 33 of duct 32.

As shown in FIG. 1C, fan, blower, or pump 38 may be disposed in communication with, and indeed may be driven by, a variable speed drive, such as a variable frequency drive (VFD) 40. Moreover, the depicted system may include a controller 44, which may be disposed in wired and/or wireless communication with the VFD 40, the load sensor(s) 42, a thermostat 46, and a user interface device 48. It should be appreciated that the functionality of the controller 44, thermostat 46, and user interface device 48 may be combined, and/or separated across each other in any desired manner. For example, a single device may function as a wireless controller of VFD 40 and wireless receiver of signals from load sensor(s) 42, while performing thermostat logic and receiving user inputs.

FIG. 1D is a schematic diagram of an exemplary fluid flow filter system 50 and environment in which embodiments of the present disclosure may be practiced. In particular, FIG. 1D depicts an air exchanger comprising an air duct 52 and any type of fluid conduit 54. Again, it should be appreciated that the fluid filtration and fluid filters of the present disclosure are applicable to any fluid system, such as a water filtration system, an oil filtration system, a refrigerant filtration system, a brake fluid filtration system, a coolant filtration system, and so on. Thus, while in one embodiment, fluid conduit 54 may carry a refrigerant or heating fluid, it should be appreciated that the embodiment of FIG. 1D is only exemplary in nature and should not be viewed as limiting of the scope of the present disclosure.

In one embodiment, the fluid filtration system of FIG. 1D includes a first fluid filter 56 and a second fluid filter 58 disposed in line with fluid conduit 54, in which fluid is driven by a fan, pump, or other impeller 60. While first fluid filter 56 and second fluid filter 58 are both depicted as being downstream from the fan, pump, or other impeller 60, it should be appreciated that the fluid filters 56, 58 may be disposed upstream, downstream, and/or upstream and downstream from the fan, pump, or other impeller 60. Like the VFD 40 and load sensor(s) 42 of FIG. 1C, the fluid filtration system 50 of FIG. 1D may be disposed in wired and/or wireless communication with a controller 44, thermostat 46, and/or user input device 48. In particular, each filter 56, 58 may include a load sensor disposed in relation to the filter such that it is configured to detect and measure an amount or extent of force imparted by the fluid filter 56, 58 on the fluid conduit 54 and/or on a conduit element or member of fluid conduit 54.

The systems of FIGS. 1C and 1D will now be described with respect to exemplary embodiments of various suitable arrangements between a filter and a load sensor, for purposes of comparison to various thresholds and alarm limits within a variable flow environment. Specifically, FIGS. 2A-2C, 3, 4A-4B, 5A-5D, and 6-8 will now depict and describe various embodiments of an arrangement between a load sensor and a filter, any of which may be applicable to the load sensor 42 and filters 34, 36, 56, 58 described with respect to FIGS. 1C and 1D.

Figure 2A:
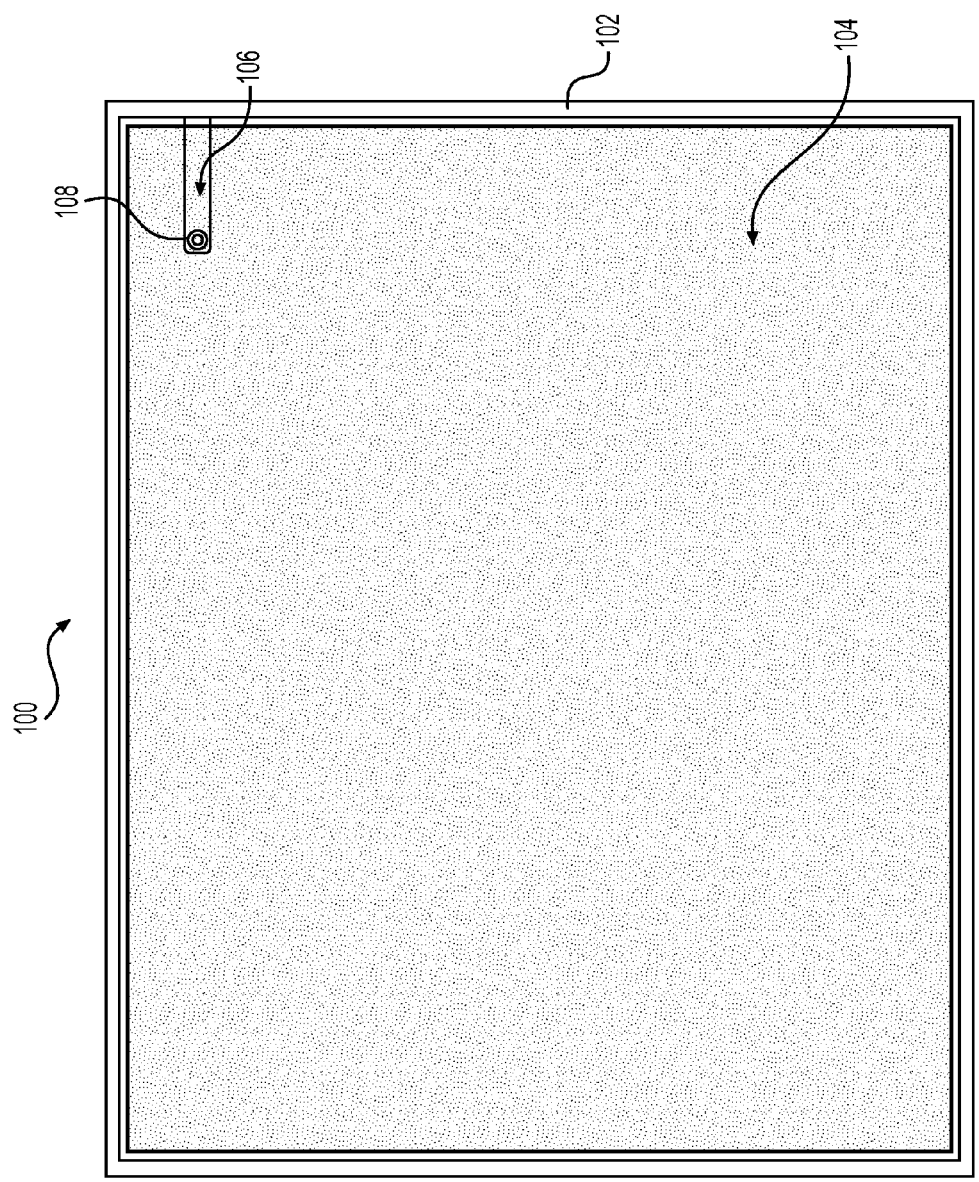
FIG. 2A is a front view illustration of a filter system, according to an exemplary embodiment of the present disclosure.
Figure 2C:
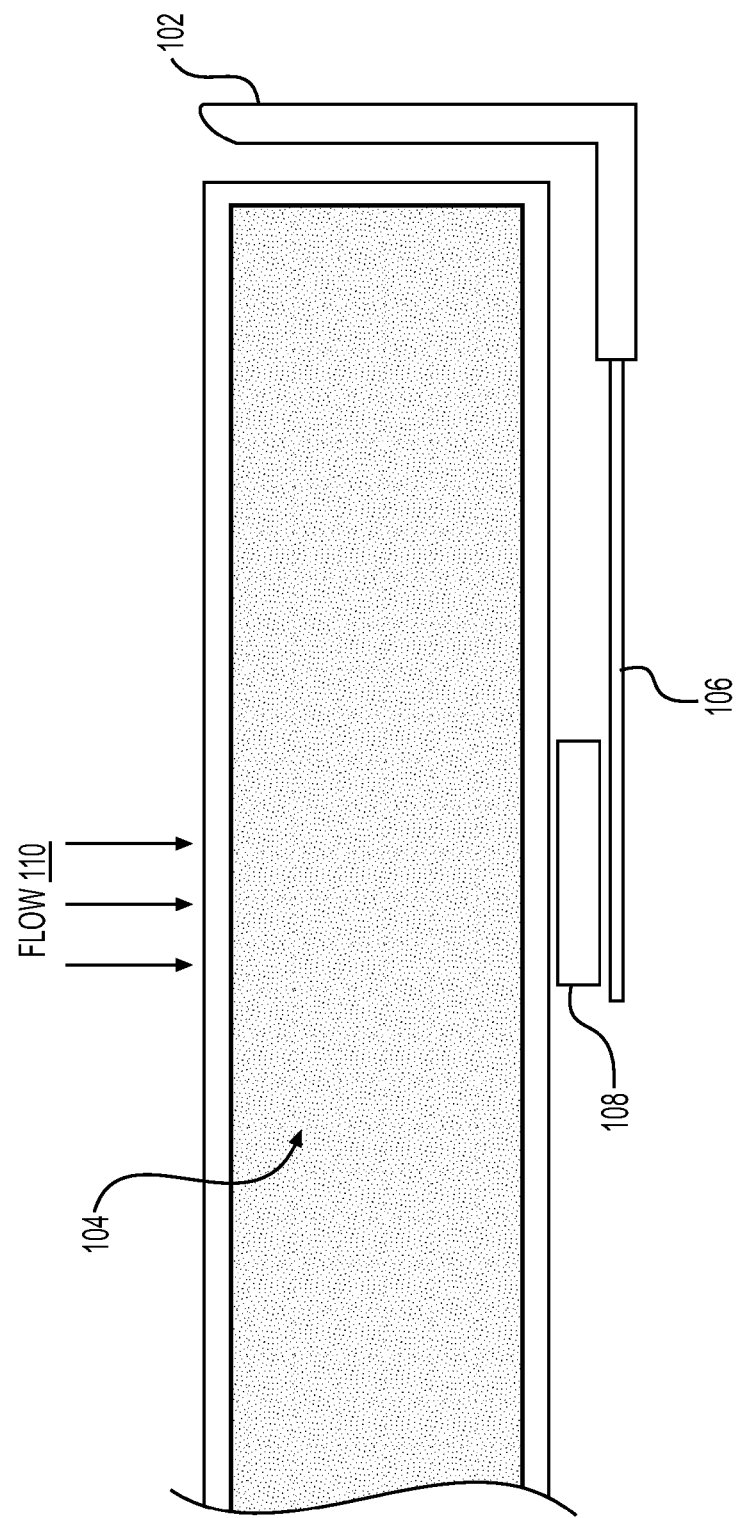

Referring now to FIGS. 2A, 2B, and 2C, a filter system 100 is shown having a housing 102 (e.g., a frame) that may support or otherwise be disposed around a filter media 104. Filter system 100 may be applicable to any filtration system described with respect to FIGS. 1A, 1B, 1C, and/or 1D, such as any filter system used in, e.g., HVAC systems, among other systems requiring air and/or fluid filtration. Filter media 104 may be any suitable media configured to remove particulate matter from a gas or fluid flow. In some embodiments, filter media 104 may be porous or have another suitable configuration. A mounting component 106 may extend from a surface of housing 102. In the embodiment shown in FIGS. 2A-2C, mounting component 106 may extend from a downstream portion of housing 102 anywhere around a perimeter of housing 102. A load sensor 108 may be disposed between filter media 104 and mounting component 106. Alternatively, load sensor 108 may be disposed between a frame or member of filter media 104 and a mounting component 106 and/or housing 102 of a filtrations system. As described above, load sensor 108 may be a load cell, strain gauge, or any other suitable sensor for measuring an amount of compression force exerted by filter media 104 (or a frame or member thereof) on mounting component 106 and/or housing 102. That is, as filter media 104 collects particulate matter, it may clog and exert a force in the direction of air/fluid/gas flow 110 that applies a force on and compresses, e.g., load sensor 108.

Load sensor 108 may communicate a signal to a receiver or other suitable device to indicate a loading condition of filter media 104. For example, as described herein, the receiver configured to receive a signal of load sensor 108 may be a component of VFD 40, controller 44, thermostat 46, and/or user interface device 48. In some embodiments, load sensor 108 may continuously send a signal to the receiver. In an alternative embodiment, load sensor 108 may send a signal only if a measured force exceeds a threshold force (e.g., indicating that the filter media 104 should be changed). In some embodiments, load sensor 108 may send a signal only in response to a request made by the receiver. It should be appreciated that the load sensor 108 (e.g., a load cell) can be connected through either a wired or wireless interface to transfer its signal to electronics and thereby trigger an alarm or some indication that it is time to change the filter. A user, such as a contractor and/or homeowner, could configure the trigger point based on the type of filter media, flow rate, an elapsed time of the increased force (to prevent false triggers due to start up) and flow density, to name a few.

Again, it should be appreciated that in the case of the load sensor 108 of system 100 (depicted in FIGS. 2A-2C, or in any other load sensor—filter arrangements of FIGS. 3-8), the depicted load sensor may be provided in communication with a variable speed drive and a controller that is configured to perform a method of determining an amount or extent of loading or clogging of the depicted filter. For example, in one embodiment, the controller may be configured to receive a value of operation of a fan or blower of a variable speed filtration (e.g., HVAC or fluid) system. The value of operation of the fan or blower may include one or more of a fan setting, a pump setting, an intensity setting, a fan speed, a rotational velocity, a voltage, a current, an air flow rate, a force, or a windspeed. The controller may be further configured to receive one or more real-time environmental conditions including one or more of a temperature measurement, a humidity measurement, an air or fluid density measurement, an altitude measurement, or an air or fluid pressure measurement of the filtration system, and modify the determined threshold filter force based on the received one or more real-time environmental conditions. The controller may further be configured to receive, from the load sensor, a value of force of a filter of the filtration system against the load sensor or another member of the filtration system. The controller may further be configured to compare the received value of force of the filter to either the received value of operation of the fan or blower, or a predetermined value of force stored in relation to the value of operation of the fan or blower. Finally, the controller may be configured to determine whether to generate a signal associated with the filter being more loaded, clogged, or dirty, than desired. In one embodiment, the controller may generate a signal associated with the filter being more loaded, clogged, or dirty, than desired, if the received value of force of the filter is outside a threshold value from the received value of operation of the fan or blower, or the predetermined value of force stored in relation to the value of operation of the fan or blower.

Figure 3:
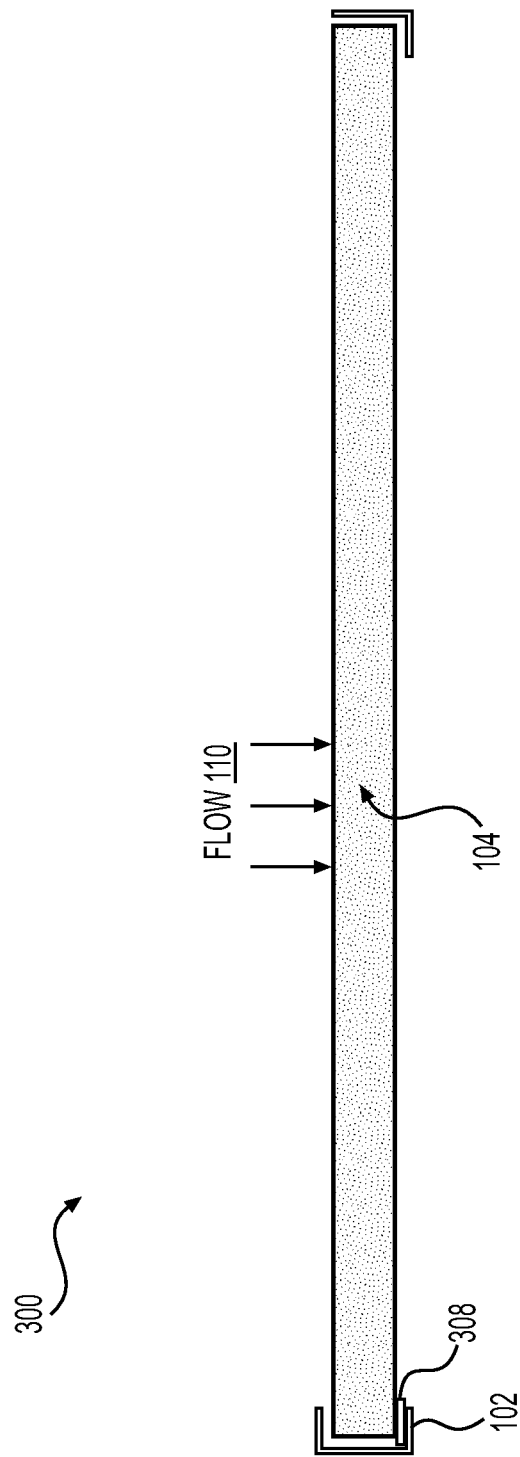
FIG. 3 is a side view illustration of another filter system, according to an exemplary embodiment of the present disclosure.

FIG. 3 depicts a filter system 300 that is substantially similar to filter system 100, except that filter system 300 may not necessarily include a mounting component 106. Instead, filter system 300 may include a load sensor 308 (e.g., that is substantially similar to sensor 108 described with reference to FIGS. 2A-2C), which may be disposed between filter media 104 and a downstream surface (e.g., a flange or lip) of housing 102 to measure a force exerted by filter media 104 on load sensor 308.

Figure 4A:
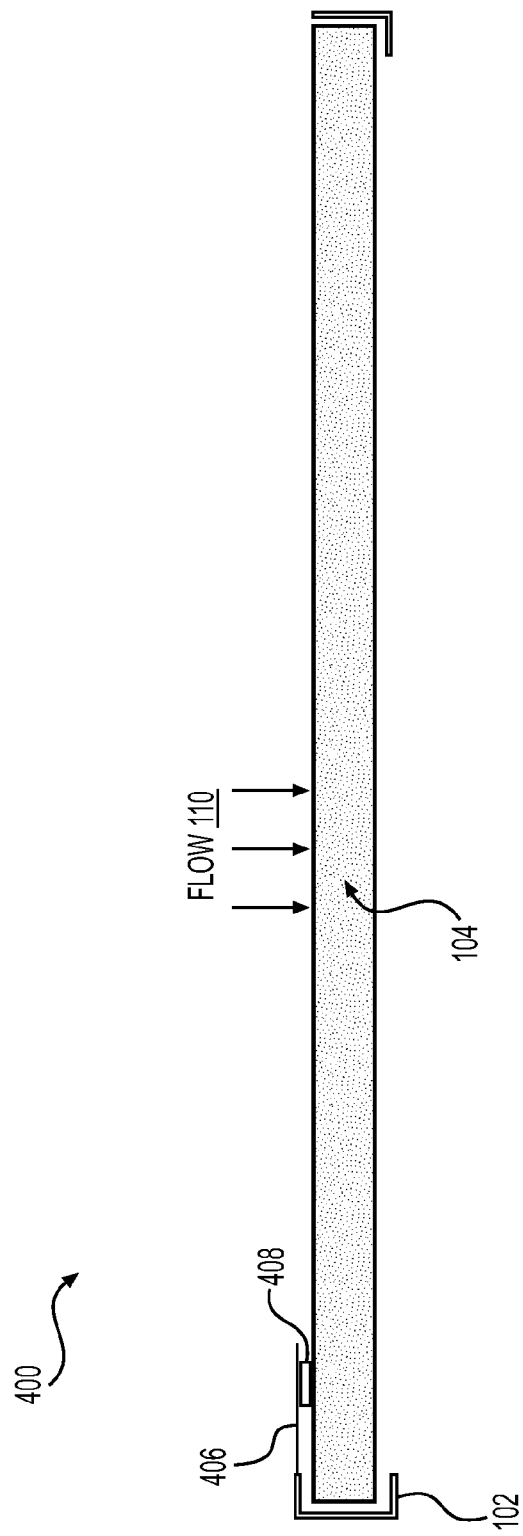

FIGS. 4A-4B depict a filter system 400 that is substantially similar to filter system 100, except that a mounting component 406 may extend from an upstream surface (e.g., a flange or lip) of housing 102. A sensor 408 (e.g., that is substantially similar to sensor 108) may be disposed between housing 102 and mounting component 408 to measure a tensile force exerted by filter media 104 in the direction of airflow 110. That is, as filter media 104 collects particulate matter, it may clog and exert a force in the direction of airflow 110 and pull on sensor 408.

FIGS. 5A-5D depict a filter system 500 that is substantially similar to filter system 400, except that filter system 500 may not necessarily include a mounting component 406. Instead, filter system 500 may include a sensor 508 (e.g., that is substantially similar to sensor 108 described with reference to FIGS. 2A-2C), which may be disposed between filter media 104 and an upstream (e.g., top) surface of housing 102 to measure a force exerted by filter media 104 on sensor 508. As shown in FIG. 5B, sensor 508 may be disposed between an upstream bracket and the filter media 104, and therefore configured to detect and measure tension caused by an increased clogging of, and reduced airflow through, the filter media 104, and therefore increasing force in a downstream direction. As shown in FIG. 5D, in one embodiment, a sensor 508 may be disposed in a channel bracket attached to the filter media 104, and therefore configured to detect either tension or compression caused by an increased clogging of, and reduced airflow through, the filter media 104, and therefore increasing force in a downstream direction.

Figure 6:
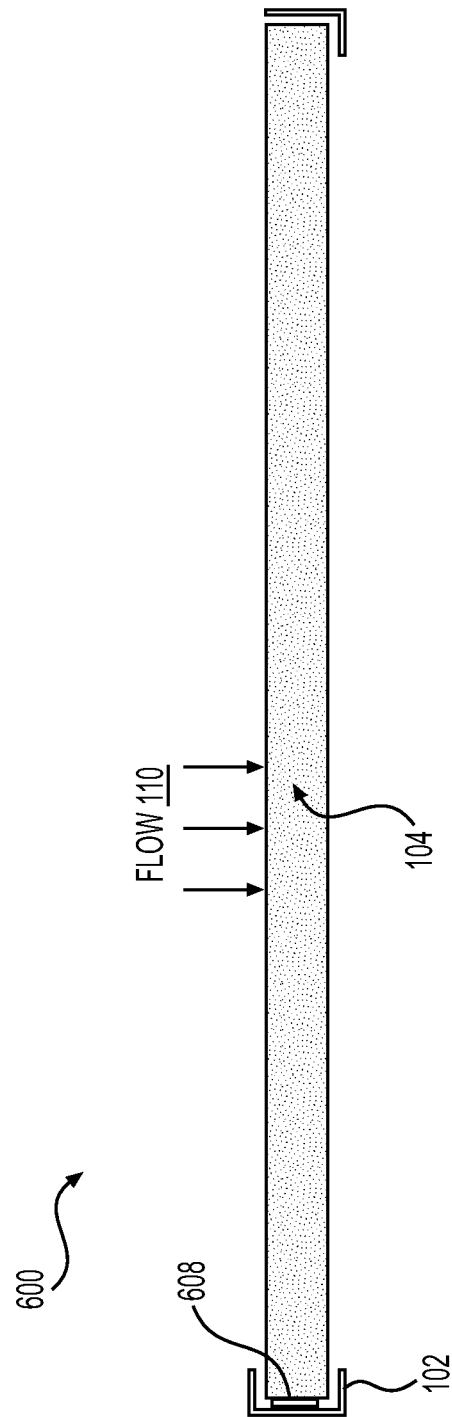
FIG. 6 is a side view illustration of another filter system, according to an exemplary embodiment of the present disclosure.

FIG. 6 depicts a filter system 600 that is substantially similar to filter system 100, except that filter system 600 may not include a mounting component 106. Instead, filter system 600 may include a sensor 608 (e.g., that is substantially similar to sensor 108 described with reference to FIGS. 2A-2C), which may be disposed between a side surface of housing 102 and a side surface of filter media 104 to measure a force exerted by filter media 104 on sensor 608. Sensor 608 may measure the force exerted by filter media 104 in multiple vectors (e.g., one or more of a downward force and an inward radial force).

Figure 7:
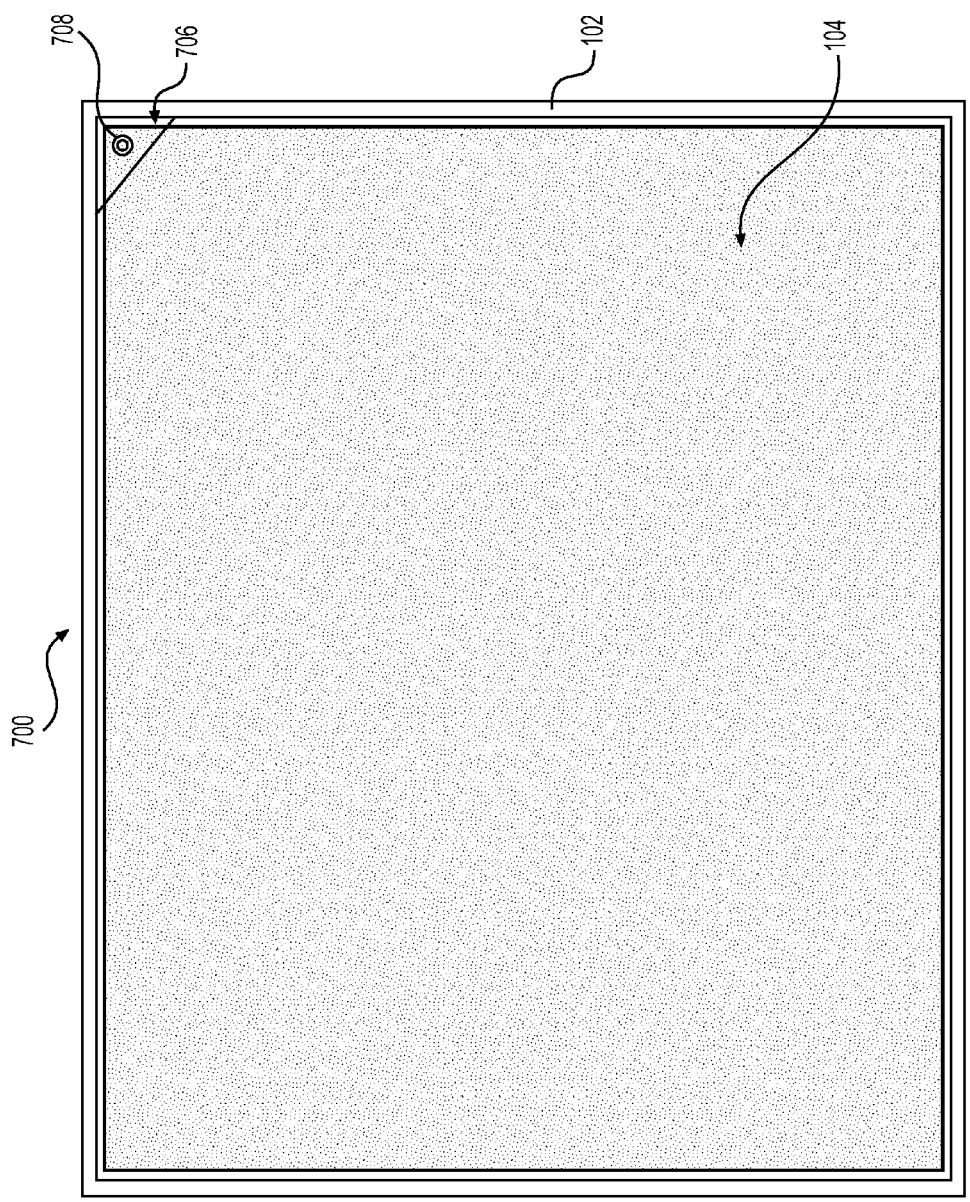
FIG. 7 is a front view illustration of another filter system, according to an exemplary embodiment of the present disclosure.

FIG. 7 depicts a filter system 700 that is substantially similar to filter system 100, except that filter system 700 may include a mounting component 706 that is coupled to one or more surfaces of housing 102 (e.g., a longitudinal side surface and a lateral side surface). Sensor 708 may be disposed between mounting component 706 and filter media 104 to measure a force exerted by filter media 104 on sensor 708. Sensor 708 may measure the force exerted by filter media 104 in multiple vectors (e.g., one or more of a tensile force, a compressive force, and an inward radial force).

Figure 8:
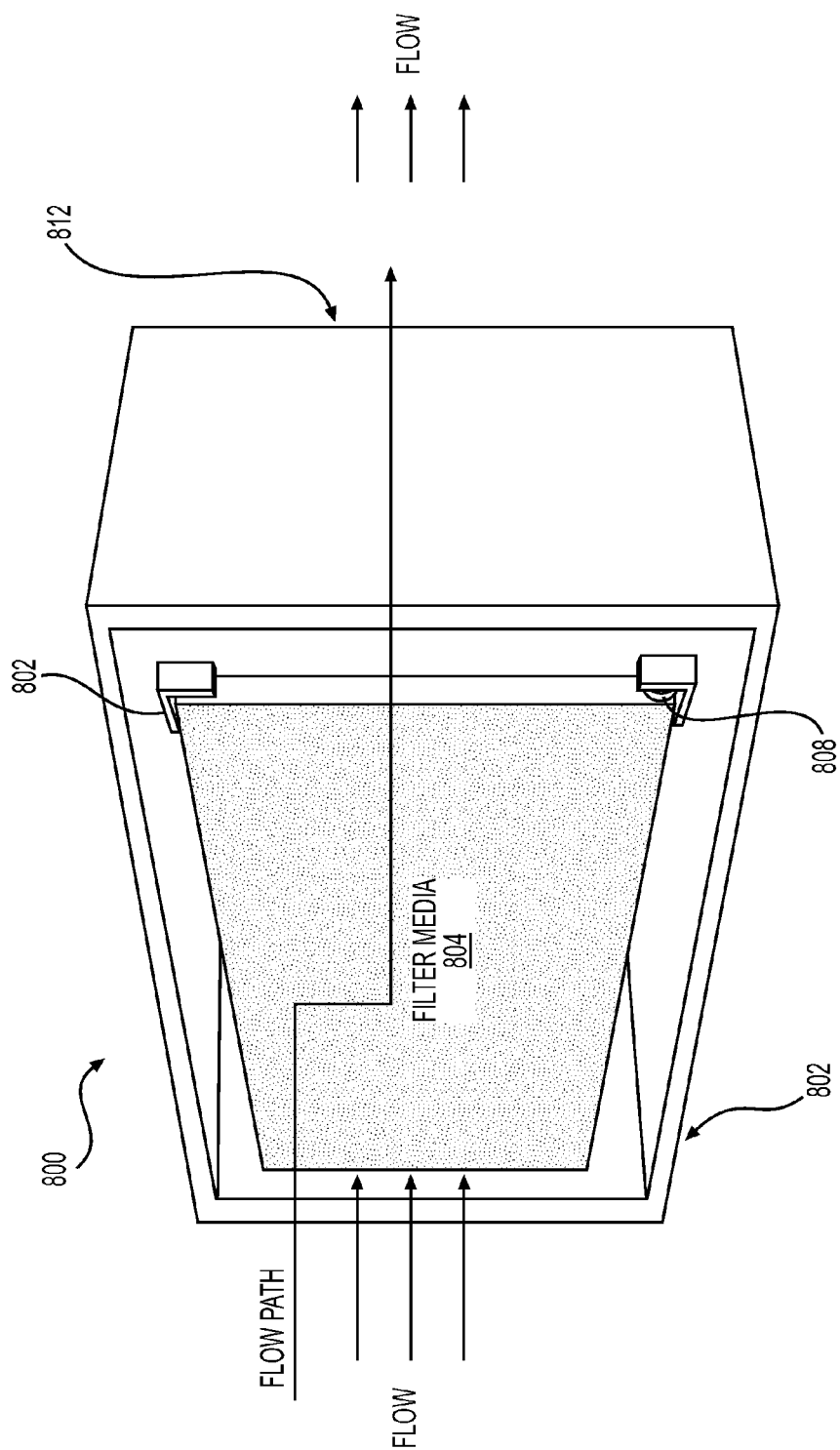
FIG. 8 is a side view illustration of another filter system, according to an exemplary embodiment of the present disclosure.

FIG. 8 depicts a filter system 800 having a housing 802 and a filter media 804. Housing 802 may be disposed within a flow path such as, e.g., a duct 801. In some embodiments, filter media 804 may be substantially conical or may be arranged in another suitable configuration. The configuration of filter media 804 may cause airflow 110 to take a non-uniform path 812 through filter media 804. A sensor 808 (that is substantially similar to sensor 108) may be disposed between filter media 804 and housing 802 at a location of housing 802 that complements or corresponds to an airflow path, e.g., an airflow path that is opposite in direction of the largest airflow vector component.

Figure 9:
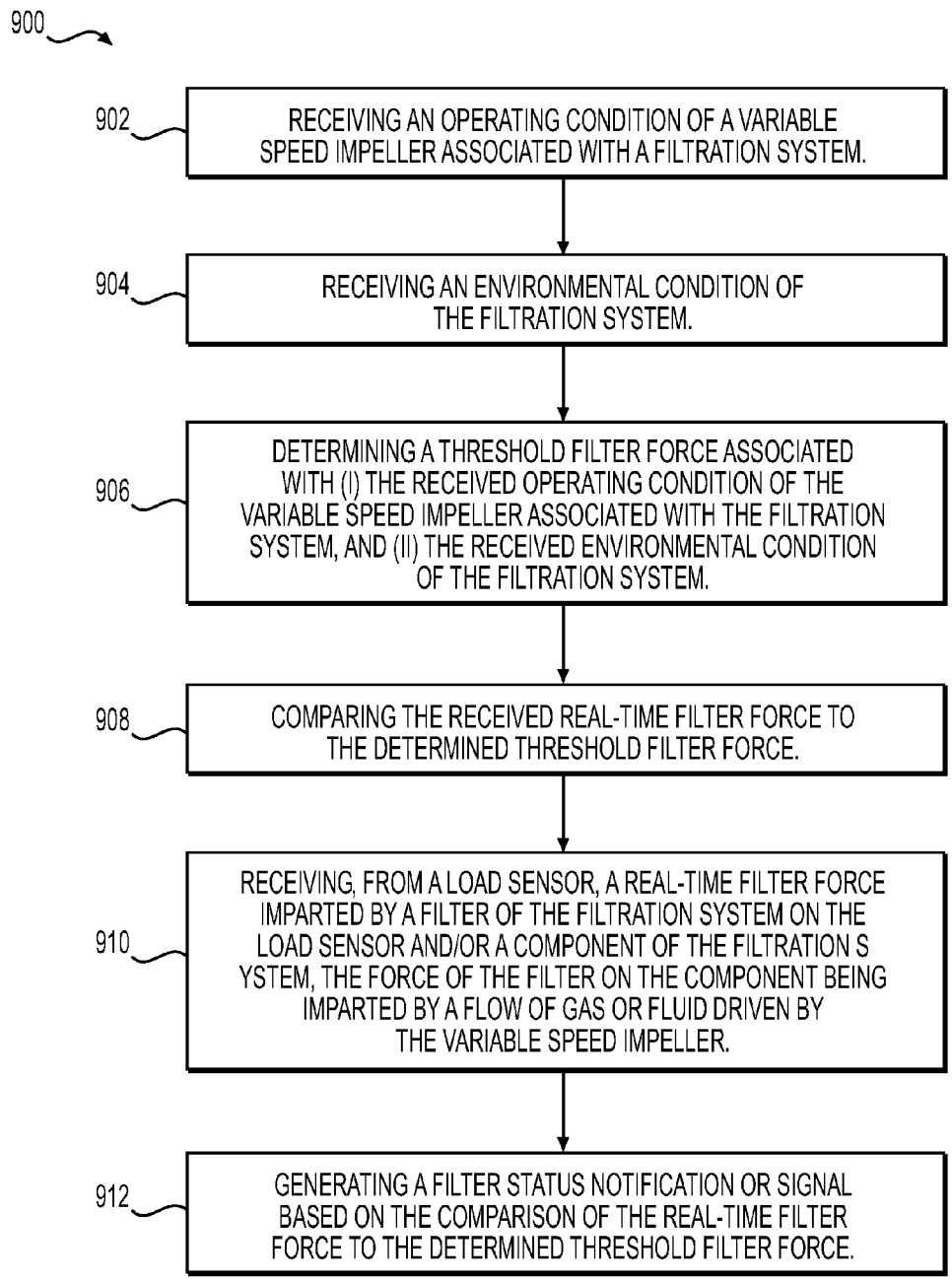
FIG. 9 is a flowchart of an exemplary method of generating a filter status notification or signal in a variable flow filtration system, according to an exemplary embodiment of the present disclosure.

Any of the systems described above with respect to FIGS. 1-8 may be used to perform any of the methods disclosed herein. In particular, any of the systems described with respect to FIGS. 1-8 may be configured to perform the exemplary methods of FIGS. 9 and 10. FIG. 9 is a flowchart of an exemplary method 900 for generating a filter status notification or signal in a variable flow filtration system, according to an exemplary embodiment of the present disclosure. As shown in FIG. 9, method 900 may include receiving an operating condition of a variable speed impeller associated with a filtration system (step 902), receiving an environmental condition of the filtration system (step 904), and determining a threshold filter force associated with (i) the received operating condition of the variable speed impeller associated with the filtration system, and (ii) the received environmental condition of the filtration system (step 906). Method 900 may further include receiving, from a load sensor, a real-time filter force imparted by a filter of the filtration system on the load sensor and/or a component of the filtration system, the force of the filter on the component being imparted by a flow of gas or fluid driven by the variable speed impeller (step 908). Method 900 may further include comparing the received real-time filter force to the determined threshold filter force (step 910), and generating a filter status notification or signal based on the comparison of the real-time filter force to the determined threshold filter force (step 912).

In one embodiment of method 900, the received operating condition may be received continuously in real-time, the one or more real-time environmental conditions may be received continuously in real-time, and the real-time filter force may be received from the load cell continuously in real-time. Alternatively, the received operating condition may be received at a first predetermined interval, the one or more real-time environmental conditions may be received at a second predetermined interval, and the real-time filter force may be received from the load cell at a third predetermined interval, wherein the first, second, and third predetermined intervals are different from each other or the same. In yet another exemplary embodiment, the real-time filter force may be received from the load cell continuously in real-time, whereas the one or more received operating conditions may be received at a first predetermined interval (e.g., every second, every 30 seconds, every minute, every 15 minutes, etc.), and the one or more real-time environmental conditions may be received at a second predetermined interval different from the first predetermined interval (e.g., a different one of every second, every 30 seconds, every minute, every 15 minutes, etc.).

Figure 10:
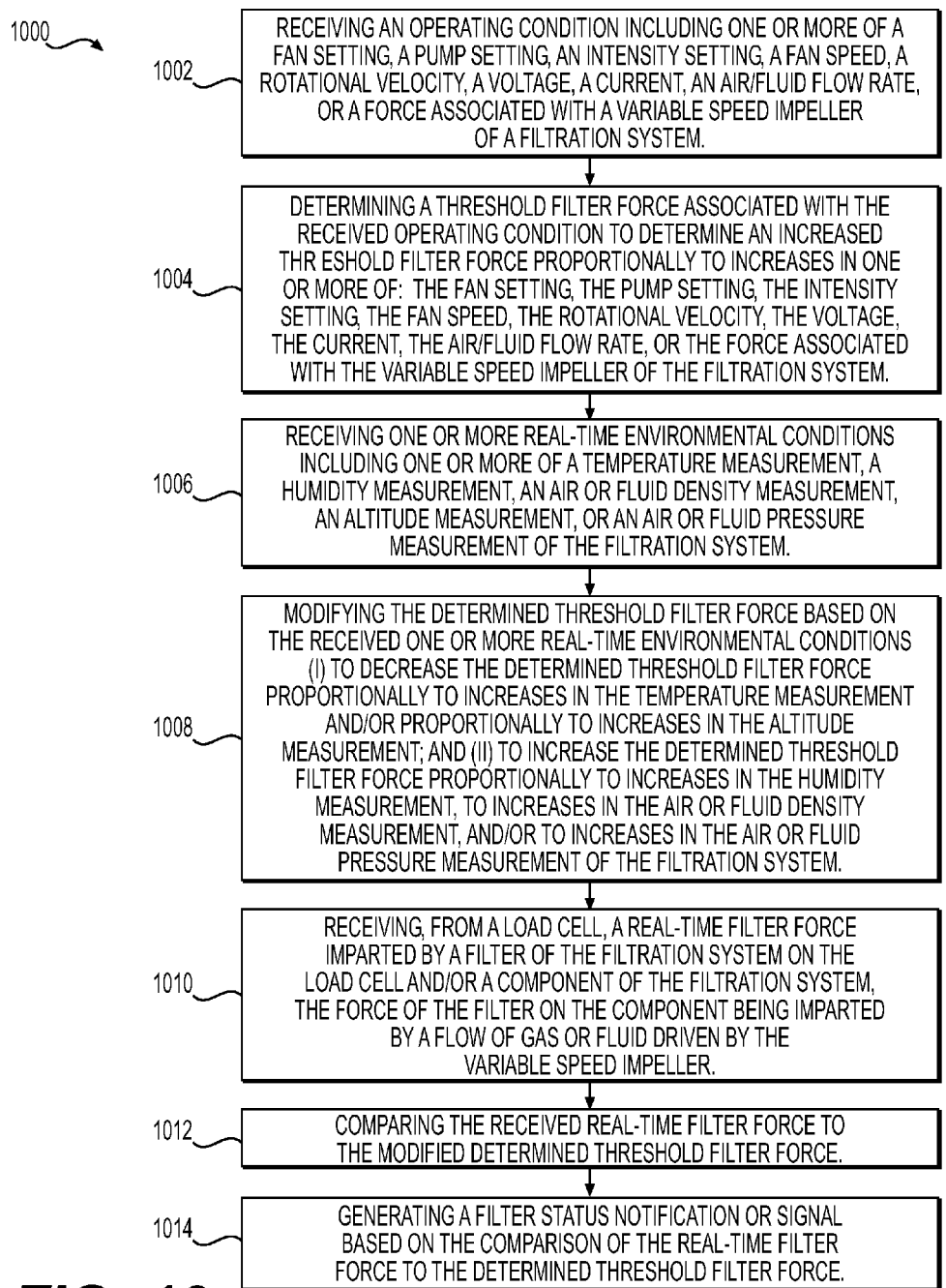
FIG. 10 is a flowchart of another exemplary method of generating a filter status notification or signal in a variable flow filtration system, according to an exemplary embodiment of the present disclosure.

FIG. 10 is a flowchart of another exemplary method 1000 of generating a filter status notification or signal in a variable flow filtration system, according to an exemplary embodiment of the present disclosure. In one embodiment, method 1000 may include receiving an operating condition a variable speed impeller of a filtration system (step 1002). For example, the operating condition may include one or more of a fan setting, a pump setting, an intensity setting, a fan speed, a rotational velocity, a voltage, a current, an air/fluid flow rate, and a force associated with the variable speed impeller of the filtration system. Method 1000 may further include determining a threshold filter force associated with the received operating condition (step 1004). For example, method 1000 may include determining an increased threshold filter force proportionally to increases in one or more of: the fan setting, the pump setting, the intensity setting, the fan speed, the rotational velocity, the voltage, the current, the air/fluid flow rate, and the force associated with the variable speed impeller of the filtration system (step 1004).

Method 1000 may further include receiving one or more real-time environmental conditions of the filtration system (step 1006). For example, method 1000 may include receiving one or more of a temperature measurement, a humidity measurement, an air or fluid density measurement, an altitude measurement, or an air or fluid pressure measurement of the filtration system. Method 1000 may further include modifying the determined threshold filter force based on the received one or more real-time environmental conditions (step 1008). For example, the determined threshold filter force may be modified so as (i) to decrease the determined threshold filter force proportionally to increases in the temperature measurement and/or proportionally to increases in the altitude measurement; and (ii) to increase the determined threshold filter force proportionally to increases in the humidity measurement, to increases in the air or fluid density measurement, and/or to increases in the air or fluid pressure measurement of the filtration system.

Method 1000 may further include receiving, from a load cell, a real-time filter force imparted by a filter of the filtration system on the load cell and/or a component of the filtration system, the force of the filter on the component being imparted by a flow of gas or fluid driven by the variable speed impeller (step 1010), comparing the received real-time filter force to the modified determined threshold filter force (step 1012), and generating a filter status notification or signal based on the comparison of the real-time filter force to the determined threshold filter force (step 1014).

Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method of generating a filter status notification or signal of a filter in a variable flow environment, the computer-implemented method comprising:

receiving an operating condition including one or more of a fan setting, a pump setting, an intensity setting, a fan speed, a rotational velocity, a voltage, a current, an air/fluid flow rate, and a force associated with a variable speed impeller of a filtration system;

determining a threshold filter force associated with the received operating condition to determine an increased threshold filter force proportionally to increases in one or more of the fan setting, the pump setting, the intensity setting, the fan speed, the rotational velocity, the voltage, the current, the air/fluid flow rate, and the force associated with the variable speed impeller of the filtration system;

receiving one or more real-time environmental conditions including one or more of a temperature measurement, a humidity measurement, an air or fluid density measurement, an altitude measurement, and an air or fluid pressure measurement of the filtration system;

modifying the determined threshold filter force based on the received one or more real-time environmental conditions (i) to decrease the determined threshold filter force proportionally to increases in the temperature measurement and/or proportionally to increases in the altitude measurement; and (ii) to increase the determined threshold filter force proportionally to increases in the humidity measurement, to increases in the air or fluid density measurement, and/or to increases in the air or fluid pressure measurement of the filtration system;

receiving, from a load cell, a real-time filter force imparted by a filter of the filtration system on the load cell and/or a component of the filtration system, the force of the filter on the component being imparted by a flow of gas or fluid driven by the variable speed impeller;

comparing the received real-time filter force to the modified determined threshold filter force; and generating a filter status notification or signal based on the comparison of the real-time filter force to the determined threshold filter force.

2. The computer-implemented method of claim 1, wherein the operating condition is received from the variable speed impeller of the filtration system.

3. The computer-implemented method of claim 1, wherein the real-time environmental condition is received from a sensor positioned in the filtration system.

4. The computer-implemented method of claim 1, wherein the received operating condition is received continuously in real-time, the one or more real-time environmental conditions are received continuously in real-time, and the real-time filter force is received from the load cell continuously in real-time.

5. The computer-implemented method of claim 1, wherein the received operating condition is received at a first predetermined interval, the one or more real-time environmental conditions are received at a second predetermined interval, and the real-time filter force is received from the load cell at a third predetermined interval, wherein the first, second, and third predetermined intervals are different from each other or the same.

6. A control system for a variable flow filtration system, the control system comprising: a digital data storage device storing instructions for generating a filter status notification or signal; and a processor configured to execute the stored instructions to perform a method comprising:

receiving, from a variable speed impeller of the variable flow filtration system, an operating condition of the variable speed impeller of the filtration system;

determining a threshold filter force associated with the received operating condition to determine an increased threshold filter force proportionally to increases in the received operating condition;

receiving one or more real-time environmental conditions of the variable flow filtration system;

modifying the determined threshold filter force based on the received one or more real-time environmental conditions;

receiving, from a load cell, a real-time filter force imparted by a filter of the variable flow filtration system on the load cell or on a component of the variable flow filtration system, the force of the filter being imparted by a flow of gas or fluid driven by the variable speed impeller;

comparing the received real-time filter force to the modified determined threshold filter force; and generating a filter status notification or signal based on the comparison of the real-time filter force to the determined threshold filter force.

7. The control system of claim 6, wherein the one or more operating conditions includes one or more of: a fan setting, a pump setting, an intensity setting, a fan speed, a rotational velocity, a voltage, a current, an air/fluid flow rate, and a force associated with the variable speed impeller of the filtration system.

8. The control system of claim 6, wherein the one or more environmental conditions include one or more of: a temperature measurement, a humidity measurement, an air or fluid density measurement, an altitude measurement, and an air or fluid pressure measurement of the filtration system.

9. The control system of claim 6, wherein modifying the determined threshold filter force based on the received one or more real-time environmental conditions comprises (i) decreasing the determined threshold filter force proportionally to increases in the temperature measurement and/or proportionally to increases in the altitude measurement; and (ii) increasing the determined threshold filter force proportionally to increases in the humidity measurement, to increases in the air or fluid density measurement, and/or to increases in the air or fluid pressure measurement of the filtration system.

10. The control system of claim 6, wherein the load cell is mounted at an upstream or downstream surface of the filter.

11. The control system of claim 6, wherein the load cell is configured to measure a compressive or tensile force exerted by the filter.

12. A variable flow filtration system comprising:
a filter disposed across a flow of fluid or gas;
a load cell disposed between the filter and a component of the variable flow filtration system;
a variable speed impeller configured to drive fluid or gas through the filter of the variable flow filtration system; and
a controller configured to:
receive, from the variable speed impeller of the variable flow filtration system, one or more operating conditions of the variable speed impeller of the filtration system;
determine a threshold filter force associated with the one or more received operating conditions to determine an increased threshold filter force proportionally to increases in the received operating condition;
receive one or more real-time environmental conditions of the variable flow filtration system;
modify the determined threshold filter force based on the received one or more real-time environmental conditions;
receive, from the load cell, a real-time filter force imparted by the filter of the variable flow filtration system on the load cell or the component of the variable flow filtration system;
compare the received real-time filter force to the modified determined threshold filter force; and
generate a filter status notification or signal based on the comparison of the real-time filter force to the determined threshold filter force.

13. The variable flow filtration system of claim 12, wherein the load cell is mounted at an upstream or downstream surface of the filter.

14. The variable flow filtration system of claim 12, wherein the load cell is configured to measure a compressive or tensile force exerted by the filter.

15. The variable flow filtration system of claim 12, wherein the received operating condition is received continuously in real-time, the one or more real-time environmental conditions are received continuously in real-time, and the real-time filter force is received from the load cell continuously in real-time.

16. The variable flow filtration system of claim 12, wherein the received operating condition is received at a first predetermined interval, the one or more real-time environmental conditions are received at a second predetermined interval, and the real-time filter force is received from the load cell at a third predetermined interval, wherein the first, second, and third predetermined intervals are different from each other or the same.

17. The variable flow filtration system of claim 12, wherein the real-time filter force is received from the load cell continuously in real-time, the one or more received operating conditions are received at a first predetermined interval, and the one or more real-time environmental conditions are received at a second predetermined interval different from the first predetermined interval.

18. The variable flow filtration system of claim 12, wherein the one or more operating conditions includes one or more of: a fan setting, a pump setting, an intensity setting, a fan speed, a rotational velocity, a voltage, a current, an air/fluid flow rate, and a force associated with the variable speed impeller of the filtration system.

19. The variable flow filtration system of claim 12, wherein the one or more environmental conditions include one or more of: a temperature measurement, a humidity measurement, an air or fluid density measurement, an altitude measurement, and an air or fluid pressure measurement of the filtration system.

20. The variable flow filtration system of claim 19, wherein modifying the determined threshold filter force based on the received one or more real-time environmental conditions comprises (i) decreasing the determined threshold filter force proportionally to increases in the temperature measurement and/or proportionally to increases in the altitude measurement; and (ii) increasing the determined threshold filter force proportionally to increases in the humidity measurement, to increases in the air or fluid density measurement, and/or to increases in the air or fluid pressure measurement of the filtration system.

* * * * *

UNITED STATES PATENT AND TRADEMARK OFFICE
CERTIFICATE OF CORRECTION

| | | |
|---|---|---|
| PATENT NO. | : 9,174,156 B2 | Page 1 of 1 |
| APPLICATION NO. | : 14/678802 | |
| DATED | : November 3, 2015 | |
| INVENTOR(S) | : William H. Scofield | |

It is certified that error appears in the above-identified patent and that said Letters Patent is hereby corrected as shown below:

Title Page, item (54) and in the Specification, Column 1, lines 1-4, "SYSTEM FOR DETERMINING FORCE IMPARTED BY A FILTER IN A VARIABLE FORCE ENVIRONMENT AND RELATED METHODS OF USE", should be replaced with -- SYSTEM FOR DETERMINING FORCE IMPARTED BY A FILTER IN A VARIABLE FLOW ENVIRONMENT AND RELATED METHODS OF USE --.

Signed and Sealed this
Twenty-second Day of March, 2016

Michelle K. Lee
*Director of the United States Patent and Trademark Office*